United States Patent
Wagner et al.

(10) Patent No.: US 11,272,837 B2
(45) Date of Patent: Mar. 15, 2022

(54) METHOD FOR PERFORMING A MOVEMENT CORRECTION WHEN MEASURING EYES, AND MEASUREMENT SYSTEM

(71) Applicant: HAAG-STREIT AG, Koeniz (CH)

(72) Inventors: Jörg Wagner, Bern (CH); Philippe Cattin, Windisch (CH); Lucio Robledo, Bern (CH)

(73) Assignee: Haag-Streit AG, Koeniz (CH)

( * ) Notice: Subject to any disclaimer, the term of this patent is extended or adjusted under 35 U.S.C. 154(b) by 0 days.

(21) Appl. No.: 17/299,136

(22) PCT Filed: Dec. 3, 2019

(86) PCT No.: PCT/EP2019/083514
§ 371 (c)(1),
(2) Date: Jun. 2, 2021

(87) PCT Pub. No.: WO2020/115052
PCT Pub. Date: Jun. 11, 2020

(65) Prior Publication Data
US 2021/0353139 A1    Nov. 18, 2021

(30) Foreign Application Priority Data
Dec. 4, 2018   (EP) .................................. 18210058

(51) Int. Cl.
*A61B 3/113*    (2006.01)
*A61B 3/10*    (2006.01)

(52) U.S. Cl.
CPC .............. *A61B 3/113* (2013.01); *A61B 3/102* (2013.01)

(58) Field of Classification Search
CPC ................................ A61B 3/113; A61B 3/102
(Continued)

(56) References Cited

U.S. PATENT DOCUMENTS 4,582,403 A * 4/1986 Weinblatt ............... A61B 3/113
351/210
4,761,071 A * 8/1988 Baron .................... A61B 3/107
351/212
(Continued)

FOREIGN PATENT DOCUMENTS

EP      2797493 A1    11/2014
WO    2013097877 A1    7/2013
WO    2013107649 A1    7/2013

OTHER PUBLICATIONS

PCT International Preliminary Report on Patentability, dated Jun. 8, 2021 and Written Opinion for International Application No. PCT/EP2019/083514 filed Dec. 3, 2019; 12 pgs.
(Continued)

*Primary Examiner* — Mohammed A Hasan
(74) *Attorney, Agent, or Firm* — Alix, Yale & Ristas, LLP (57) ABSTRACT

The invention relates to a method for performing a movement correction when measuring a human eye, in which the eye is scanned by a measurement beam in order to obtain a set of position values of an eye structure. Scanning extends over a measurement time interval, wherein the position values are each provided with a timestamp within the measurement time interval. A surface shape and a displacement function are determined, with the displacement function representing a movement pattern during the measurement time interval, and the surface shape and the displacement function being determined in such a way that the position values are approximated by the surface shape when the surface shape is moved according to the displacement function. Moreover, the invention relates to an associated measurement system.

12 Claims, 2 Drawing Sheets

(58) Field of Classification Search
USPC .......................................................... 351/209
See application file for complete search history.

(56) References Cited

U.S. PATENT DOCUMENTS

| | | | |
|---|---|---|---|
| 5,928,221 A * | 7/1999 | Sasnett | A61F 9/00802 |
| | | | 606/5 |
| 7,365,856 B2 | 4/2008 | Everett et al. | |
| 2017/0258318 A1* | 9/2017 | Wagner | A61B 3/102 |
| 2018/0192866 A1 | 7/2018 | Abou Shousha et al. | |

OTHER PUBLICATIONS

Hansford C. Hendargo et al., "Automated non-rigid registration and mosaicing for robust imaging of distinct retinal capillary beds using speckle variance optical coherence tomography", Biomedical Optics Express, vol. 4, No. 6, published May 7, 2013, XP055295793, DOI: 10.1364/BOE.4.000803, ISSN: 2156-7085, 20 pgs.

PCT International Search Report and Written Opinion for Application No. PCT/EP2019/083514 filed Dec. 3, 2019; dated Apr. 2, 2020; 15 pgs.

* cited by examiner

METHOD FOR PERFORMING A MOVEMENT CORRECTION WHEN MEASURING EYES, AND MEASUREMENT SYSTEM

BACKGROUND

The invention relates to a method for performing a movement correction when measuring eyes. The invention additionally relates to an associated measurement system.

In the case of measurements on the eye, the measurement result can be corrupted if the eye moves during the recording of the measured values. The more time the measurement occupies, the stronger the effects the movements of the eye have. A longer measuring duration results in particular when scanning the eye using a measuring beam, as is typically the case in OCT measurements, for example.

One possible procedure is first to record a rapid reference measurement over the measurement region, during which the measuring duration is so short that the measurement is not corrupted by movements of the eye. The following longer measurements having a greater number of support points can be adjusted on the basis of the first measurement to eliminate the movement from the data U.S. Pat. No. 7,365,856 B2, EP 2 797 493 A1. The disadvantage in this procedure is that the entire measurement result can be corrupted by an inaccuracy in the reference measurement. In addition, a rapid scanning system is necessary to be able to execute the reference measurement sufficiently rapidly.

Alternatively, multiple rapid measurements can also be recorded, which are then adjusted to one another. The requirement for this is that a meaningful geometry of the eye (for example a meridian) is recorded sufficiently rapidly within one measurement, so that the eye movement therein can be neglected. A rapid system having rapid data acquisition and rapid scanner is also required for this purpose.

SUMMARY OF THE INVENTION

The invention is based on the object of presenting a method and a measurement system for performing a movement correction when measuring eyes, which have a reduced susceptibility to error. Proceeding from the cited prior art, the object is achieved by the features of the independent claims. Advantageous embodiments are specified in the dependent claims.

In the method according to the invention, the eye is scanned using a measuring beam to obtain a set of position values of an eye structure. The scanning extends over a measurement period, wherein the position values are each provided with a timestamp within the measurement period. A surface shape and a displacement function are ascertained, wherein the displacement function represents a movement sequence during the measurement period. The surface shape and the displacement function are ascertained in such a way that the position values are approximated by the surface shape when the surface shape is moved according to the displacement function.

The invention starts from the assumption that the movement which the eye has performed within the measurement period can be described by a displacement function. In an ideal case, the measurement is free of measurement errors, a surface shape is found which corresponds to the actual shape of the eye structure, and a displacement function is found which corresponds to the actual movement sequence of the eye. If this surface shape is displaced in accordance with this displacement function, all position values recorded of the eye structure thus lie on the surface shape (with suitable mutual adjustment of spatial and chronological coordinate systems). In contrast to the prior art, a reference measurement is not required as a starting point for the movement correction. This is particularly advantageous if the scanning system does not have the required speed to carry out a low-movement reference measurement.

In practice, measurement errors occur and deviations arise both between the surface shape and the actual shape of the eye structure and also between the displacement function and the actual movement sequence. The wording that the position values are "approximated" by the surface shape takes into consideration this deviation between ideal and practically performed method. If the method were performed in ideal form, the position values and the surface shape would correspond identically. Approximate in the meaning of the invention means ascertaining the surface shape and the displacement function so that the position values are approximated in the scope of the boundary conditions of the practically performed measurement. For example, a quality criterion can be specified for the approximation, and the surface shape and the displacement function can be ascertained so that the deviation established on the basis of the quality criterion is less than a specified threshold value. When reference is made in the following description to position values which lie on the surface shape, this is thus equivalent to an approximation in this meaning.

If one considers a first time and a second time within the measurement period, a movement sequence which describes the movement of the eye between the two times thus results from the displacement function. A surface shape which correctly reproduces the actual shape of the eye structure and which is displaced according to the displacement function can be represented jointly with the position values obtained during the measurement in a coordinate system so that the surface shape lies on the position value obtained using the measurement for both times. Joint representation of the surface shape and the position values in a coordinate system means that the spatial coordinates of the surface shape and the position values are adjusted correctly in relation to one another, and the chronological sequence of the displacement function is matched with the timestamps of the position values. The wording that the surface shape and the position values are displaced in relation to one another in accordance with the displacement function does not include a restriction to a specific form of representation of the spatial and chronological coordinates. Various forms of movement representations, difference specifications over time, and the like are possible. A time within the measurement period can be selected as the reference time, starting from which the relative coordinates are defined.

The method can be performed so that all position values which have a timestamp between the first time and the second time lie on the surface shape displaced according to the displacement function. The number of the position values between the first time and the second time can be greater than 1000, preferably greater than 5000, more preferably greater than 20 000. The first time can coincide with the beginning of the measurement period. The second time can coincide with the end of the measurement period. It is also possible that the period between the first time and the second time corresponds to a section of the measurement period.

The ascertainment of the surface shape and/or the ascertainment of the displacement function can consist of various surface shapes or displacement functions being tested out and it being established on the basis of the quality criterion which combination of surface shape and displacement function best approximates the position values. All position values recorded in the measurement period or a subset of these position values can be approximated. The surface shape and displacement function in which the deviation from the position values is smallest can be assumed as the best possible approximation to the position values. The relevant surface shapes and/or displacement functions can be selected in the scope of an optimization method. The surface shapes and/or displacement function can be selected randomly, for example, and it can be established according to the method of least squares which combination of displacement function and surface shape best approximates the position values.

The surface shape thus ascertained can be viewed as a movement-corrected representation of the shape of the scanned surface and output as the result of the method. Alternatively, it is also possible to perform a correction of the position values on the basis of the displacement function and to ascertain the shape of the scanned surface on the basis of the corrected set of position data.

Position values approximated using the displacement function can be corrected for this purpose on the basis of the displacement function, so that a corrected set of position values results. A surface function can be ascertained which approximates the corrected set of position values. The surface function can be output as a representation of the shape of the scanned eye structure. The output can consist, for example, of the surface function being displayed in a mathematical or graphic representation on a display screen, the surface function being stored in a memory or output, or the surface function being transferred to a downstream module for further processing. This list is not exhaustive.

The displacement function can be represented as a time-dependent polynomial. One possibility is to view the movement sequence as a superposition of translational movements along the three axes of a Cartesian coordinate system and to associate a time-dependent polynomial with each of the three axes. At small amplitudes, rotational movements can be viewed as superpositions of translational movements. In one refinement of the invention, rotational movements can also be directly approximated by suitable mathematical functions.

The Z axis of the coordinate system can be aligned in parallel to the direction of the measuring beam. The measuring beam can be oriented on the eye in parallel to the optical axis. The polynomial associated with the Z axis can be of a higher degree than the polynomial of the X axis and/or the polynomial of the Y axis. The degree of the polynomial of the Z axis can be, for example, between 4 and 8.

The coefficients of the displacement function can be obtained by solving an optimization task. The criterion for the optimization can be that the difference between the surface shape, in consideration of its chronological position derived from the displacement function, and the position values ascertained using the measurement is as small as possible. This criterion is preferably applied to all position values simultaneously. The optimization problem can be solved, for example, according to the method of least squares.

In one embodiment, the set of position values is divided into a plurality of chronologically successive chunks. The movement sequence during the duration of one chunk can be described by a section function, wherein the section function can be ascertained in the same way as described above for the displacement function. In one embodiment, a section function is ascertained for each chunk. The displacement function can result by concatenating the section functions. The displacement function can be a piecemeal polynomial function (spline).

For the compilation of the displacement function from section functions, a regularization can be specified in order to ensure that the simplest or most plausible shape is found, using which the shape of the eye structure and the time-dependent translation can be described. The regularization can comprise one or more of the following aspects. The position of a section function, for example of the chronologically first section function, can be fixed within the space to prevent the entire set of position values from being able to be displaced within the space without the approximation error changing. The displacement function can be regularized so that an average displacement of zero results over all section functions. The displacement function can be regularized so that the transition between two chronologically adjacent section functions is continuous. The displacement function can be regularized so that in the first derivative of the displacement function, a continuous transition between two chronologically adjacent section functions results.

The surface shape, using which the position values are approximated, can also be represented by a mathematical function. An example of an eye structure to which the position values can relate is the surface of the cornea. One possible application of the method according to the invention is that the surface shape corresponds to a topography of the cornea. The cornea and also other structures of the eye in which the method can be applied have a circular shape. Therefore, Zernike polynomials, which are polynomials defined within the unit circle, can be used as the mathematical function for representing the eye structure. The area covered by the Zernike polynomials can be adapted by scaling to the size of the examined eye structure.

To perform the movement correction, it is not necessary to represent the surface shape in the highest possible mathematical accuracy. It can be sufficient to depict the surface shape by lower-order Zernike polynomials, for example up to the fourth order, up to the sixth order, or up to the eighth order.

To ascertain the surface shape, an optimization problem can be formulated in which the surface shape and the displacement function are jointly varied. If the surface shape is described by Zernike polynomials, the coefficients of the Zernike polynomials can thus be ascertained in this way. There can be a uniform optimization procedure, within which both the coefficients of the polynomials of the displacement function and also the coefficients of the Zernike polynomials are ascertained. An approximation both with regard to the surface shape and also with regard to the movement sequence during the measurement period is thus performed using one optimization step.

The measuring beam, using which the eye is scanned, can be an OCT measuring beam. In OCT measurements, short-coherence OCT light is split into an object beam path and a reference beam path. The object beam path is conducted as the measuring beam onto the object. Components of the OCT light backscattered from the object are brought into interference with the light of the reference beam path. Scattering centers in the object can be concluded from the interference pattern. The OCT light source can be a swept source light source.

A plurality of A-scans can be obtained using the measuring beam. A measurement which extends in the direction of the measuring beam into the depth of the object is referred to as an A-scan. An item of information about the axial position of an eye structure which is sought can be derived from such an A-scan. For example, if the eye structure which is sought is the surface of the cornea, this information can thus be obtained from the A-scan. Such an item of information about the axial position of an eye structure derived from an A-scan results together with the position of the A-scan in a position value of the eye structure. The set according to the invention of position values of the eye structure can be obtained by a plurality of A-scans. The set of position values forms a point cloud, in which each point lies on a surface of the eye structure.

Before the ascertainment of the displacement function and possibly the mathematical function of the surface shape, implausible measured values can be deleted from the set of position values. For example, it is possible in the case of the measurement on the eye that the patient blinks during the measurement and the measurement beam therefore is incident on the eyelid instead of on the surface of the cornea. The chunks can be defined so that they extend over a specific time, so that the same number of position values is contained in the starting point in all chunks. After implausible measured values are deleted, the number of the position values can differ between the chunks. Empty chunks in which no position values are contained can also result in this way. Empty chunks are taken into consideration during the compilation of the displacement function from section functions in that two chunks between which an empty chunk is arranged are not considered to be adjacent chunks.

The scanning pattern with which the measuring beam scans the eye can be selected so that measurement data from the entire examined eye structure are contained in each chunk. In other words, it can be true for each of the chunks that within the area scanned by the measuring beam, every circle which covers an area of greater than 10%, preferably greater than 5%, more preferably greater than 2% within the scanned area contains at least one measured value. This applies for the state before implausible measured values have been deleted.

The scanning of the eye using the measuring beam can be carried out so that the measuring beam is deflected in the lateral direction, so that it describes a curve on the surface of the eye. The desired sequence of A-scans can be recorded along the curve.

The curve can be formed so that abrupt direction changes, which represent a high stress for the scanning device, are avoided. For example, the curve can have the following shape.

$$P_{SP}(t) = \begin{pmatrix} x_{SP}(t) \\ y_{SP}(t) \end{pmatrix} = R_{SP} \sin(a\omega t) \begin{pmatrix} \sin(b\omega t) \\ \cos(b\omega t) \end{pmatrix}$$

In this case, $R_{SP}$ is the radius of the scanned surface and $\omega = 2\pi/T$ is the base frequency of the scanning derived from the period duration T. The period T within which the scanning pattern is passed through once is referred to as the period T. The ratio between the frequencies is defined by the scalars a and b. The radius $R_{SP}$ of the scanned surface can be, for example, between 2 mm and 8 mm, preferably between 3 mm and 6 mm. The scalar b can be greater by a factor between 1.2 and 4, preferably between 1.5 and 3 than the scalar a. The scalar a can be, for example, between 10 and 20, the scalar b between 20 and 40. The period duration T, within which the scanning pattern is passed through once, can be, for example, between 0.2 seconds and 1 second. If the curve is passed through at constant speed $\omega$, the recorded position values are thus distributed more densely in certain regions of the scanned structure and distributed less densely in other regions. In one embodiment of the invention, the speed w is varied during the passage to achieve a better uniform distribution of the position values on the scanned structure.

During the scanning of the eye using the measuring beam, it is possible to pass through the curve multiple times, for example between twice and ten times. In one embodiment, the curve is passed through along the identical path multiple times, as is possible, for example, if the starting point and the end point of the curve are identical. Embodiments are also comprised in which the curves are identical with respect to the pattern, but are displaced or rotated relative to one another.

It is advantageous if the curve which the measuring beam describes on the scanned eye structure has a greater number of intersection points. The number of the intersection points can be, for example, greater than 50, preferably greater than 100, more preferably greater than 400. This applies to a single pass through the curve. In the case of multiple passes through the curve, the number of the intersection points can increase accordingly. Such intersection points can be helpful when ascertaining the displacement function. In this context, it is furthermore advantageous if the position values are recorded so that they meet the intersection points as well as possible. During one pass of the curve, for example, between 2000 and 50 000 A-scans, preferably between 10 000 and 20 000 A-scans can be recorded. A chunk can extend, for example, over 1000 to 25 000 A-scans, preferably 5000 to 10 000 A-scans. The set of position values can be divided, for example, into 4 to 20, preferably 5 to 10 chunks.

The sequence of the method according to the invention will be described hereinafter on the basis of an example, in which the displacement function and the surface shape are approximated simultaneously and in which the displacement function is compiled as a piecemeal polynomial from a plurality of section functions. The steps mentioned hereinafter can be applied individually or in combination in the scope of the invention. The set of position values of the eye structure ascertained using the measuring beam can be used as the input variable for the optimization method, wherein the implausible measured values were preferably previously excluded.

The set of position values is provided in the form of coordinates $P_n = (x_n, y_n, z_n)^T$ and timestamps $t_n$ with $n=0, 1, \ldots, N^{t-1}$, wherein $N_t$ denotes the total number of the points. The set of position values is split into a plurality of chunks, wherein the chunks can extend, for example, over a period between 0.05 seconds and 0.2 seconds. The time span covered by the individual chunks can be identical. The number of position values contained in the chunks can differ from one another after the deletion of implausible measured values. Chunks which are entirely free of plausible position values can be completely deleted and only still taken into consideration in the further optimization method in that two chunks between which an empty chunk was deleted are not considered to be adjacent chunks. A number of Z* valid chunks results.

The piecemeal polynomial displacement of the chunks can be defined by the following function f(t):

$$f(t) = \begin{pmatrix} f_x(t) \\ f_y(t) \\ f_z(t) \end{pmatrix} = \sum_{i=0}^{Z^*-1} \text{boxchar}_i(t) \begin{pmatrix} \alpha_{i0}^x 1 + \alpha_{i1}^x(t-t_i^m)^1 + \ldots + \alpha_{iO_x}^x(t-t_i^m)^{O_x} \\ \alpha_{i0}^y 1 + \alpha_{i1}^y(t-t_i^m)^1 + \ldots + \alpha_{iO_y}^y(t-t_i^m)^{O_y} \\ \alpha_{i0}^z 1 + \alpha_{i1}^z(t-t_i^m)^1 + \ldots + \alpha_{iO_z}^z(t-t_i^m)^{O_z} \end{pmatrix}$$

In this case, tim denotes the average time of the position values in the chunk i, and α are the coefficients of the individual polynomials. The boxchar function boxchari(t) is equal to 1 if t is within the chunk interval i, and is equal to 0 if t is outside this interval. $O_x=6$, $O_y=6$, and $O_z=8$ denotes the degree of the displacement polynomials in the relevant axis. The axis parallel to the measuring beam is referred to as the Z axis. The X axis and Y axis are orthogonal thereto.

The coefficients of the displacement polynomials are determined by solving the following approximation problem of the least average squares:

$$\underset{\beta,p}{\text{minimize}} \left\| \begin{pmatrix} Z & M \\ 0 & C \end{pmatrix} \begin{pmatrix} \beta \\ \alpha \end{pmatrix} - \begin{pmatrix} z \\ 0 \end{pmatrix} \right\|_2^2$$

In this case, β is a series vector with the Zernike coefficients and α is a series vector with the coefficients of the displacement polynomials. The columns of the matrix Z contain the Zernike polynomials which were recorded at the x, y coordinates, while z represents the Z coordinates of the position values. The matrix M contains the polynomial basic function for the displacement in each chunk and α the corresponding coefficients:

$$M = \begin{pmatrix} M_0 & 0 & \cdots & 0 \\ 0 & M_1 & \ddots & 0 \\ \vdots & \ddots & \ddots & \vdots \\ 0 & 0 & \ddots & M_{Z^*-1} \end{pmatrix}$$

$$\alpha = (\alpha_0 \quad \alpha_1 \quad \cdots \quad \alpha_{Z^*-1})^T$$

$M_i$ contains the displacement basic function in all three axes and $\alpha_i$ are the coefficients of the displacement polynomials in all three axes for the specific chunk$_i$.

$$M_i = (M_i^x \, M_i^y \, M_i^z)$$

$$\alpha_i = (\alpha_i^x \, \alpha_i^y \, \alpha_i^z)^T = (\alpha_{i0}^x \ldots \alpha_{iO_x}^x \ldots \alpha_{iO_y}^y \, \alpha_{i0}^z \ldots \alpha_{iO_z}^z)^T$$

The columns of $M_i^x$, $M_i^y$, $M_i^z$ represent the displacement basic functions in the relevant directions. The displacement basic functions for the x and y directions are estimated on the basis of an initial Zernike fit on the cloud of position values. The order of the Zernike fit can be, for example, between 4 and 8, preferably 6. Each entry is ascertained by partial derivation of the Zernike surface at the x, y coordinates of the relevant points n and order m.

$$M_{i\,n,m}^x = \frac{d}{dx} Z(x_n, y_n) \times (t_n - T_i)^m$$

$$M_{i\,n,m}^y = \frac{d}{dy} Z(x_n, y_n) \times (t_n - T_i)^m$$

For the Z direction, this simplifies to:

$$M_{i\,n,m}^z = (t_n - T_i)^m$$

A regularization matrix C is introduced to penalize discontinuities in the displacement and its first derivative and to penalize the offset of the regularization. The penalization of discontinuities is restricted to adjacent chunks. Successive chunks are considered to be adjacent if an empty chunk between them was not removed.

$$C = \begin{pmatrix} R(t_0^l - t_0^m) & -R(t_0^l - t_1^m) & 0 & \ddots & 0 & 0 \\ 0 & R(t_1^c - t_1^m) & -R(t_1^c - t_2^m) & \ddots & 0 & 0 \\ \ddots & \ddots & \ddots & \ddots & \ddots & \ddots \\ 0 & 0 & 0 & \ddots & -R(t_{Z^*-3}^c - t_{Z^*-2}^m) & 0 \\ 0 & 0 & 0 & \ddots & R(t_{Z^*-2}^c - t_{Z^*-2}^m) & -R(t_{Z^*-2}^c - t_{Z^*-1}^m) \\ S & 0 & 0 & \cdots & 0 & 0 \end{pmatrix}$$

The R matrices contain the displacement basic functions and their first derivatives at the intersections of adjacent chunks for each direction.

$$R(t) = \begin{pmatrix} R^x(t) & 0 & 0 \\ 0 & R^y(t) & 0 \\ 0 & 0 & R^z(t) \end{pmatrix}$$

$$R^x(t) = \begin{pmatrix} 1 & t & t^2 & \cdots & t_x^O \\ 0 & 1 & 2t & \cdots & O_x t^{O_x-1} \end{pmatrix}$$

$$R^y(t) = \begin{pmatrix} 1 & t & t^2 & \cdots & t_y^O \\ 0 & 1 & 2t & \cdots & O_y t^{O_y-1} \end{pmatrix}$$

$$R^z(t) = \begin{pmatrix} 1 & t & t^2 & \cdots & t_z^O \\ 0 & 1 & 2t & \cdots & O_z t^{O_z-1} \end{pmatrix}$$

Without the regularization, the problem would be underdefined and the entire cloud of position values could be displaced without influence on the approximation error. With the matrix S, the offset of the first chunk $\alpha_0^x{}_0 \, \alpha_0^z{}_0$ is set to zero, whereby a displacement of the complete surface is prevented.

$$S = s_{reg} \begin{pmatrix} 1 & 0 & 0 & 0 & \cdots & 0 \\ 0 & 1 & 0 & 0 & \cdots & 0 \\ 0 & 0 & 1 & 0 & \cdots & 0 \end{pmatrix}$$

The scalar $s_{reg}$ defines the strength of the regularization.

After the solution of the least square problem, the position values are corrected by subtraction of the established displacement from the point coordinates.

$$P_n^* = P_n - f(t_n) \text{ for } n=0,1,\ldots N^T-1$$

After the displacement function has been ascertained, a quality check can be performed. If the optimization method was carried out on the basis of N chunks, N different subsets, which each comprise N−1 chunks, can thus be formed by excluding individual chunks in each case.

The coefficient standard deviation of a Zernike reconstruction can be determined for each of the subsets. The degree of the Zernike reconstruction can be higher than the degree of the Zernike reconstruction when ascertaining the displacement function, in particular the degree can be increased by 1. For example, a Zernike reconstruction of the seventh degree can be performed. If the least coefficient standard deviation for one of the subsets is less than the coefficient standard deviation over all chunks, the relevant subset can thus take the place of the prior entirety of the data. As a result of the quality check, it is thus possible to continue with a reduced set of position values, in which the position values of one chunk are deleted. The quality check can be iteratively continued until the coefficient standard deviation of the (remaining) overall data is less than the coefficient standard deviation of each of the subsets.

The shape of the eye structure (for example the topography of the cornea surface) can be reconstructed on the basis of the position values, which were corrected on the basis of the displacement function. For this purpose, a Zernike reconstruction can be applied to the corrected position values. The degree of the Zernike reconstruction can be higher than the degree of the Zernike polynomials, using which the surface shape is represented when ascertaining the displacement function. For example, a Zernike reconstruction can be carried out using Zernike polynomials up to the $10^{th}$ degree.

Further items of information valuable to the user can be derived therefrom, for example curvature maps of the cornea front side and rear side and a map representation of the cornea thickness. Movement-corrected sectional images can also be calculated, or other eye structures, for example the eye lens, can be measured free of movement.

The invention additionally relates to an associated measurement system. The measurement system comprises a measuring beam and a scanning device to deflect the measuring beam in the lateral direction. Using a detector, a set of position values of an eye structure is provided from a signal generated by the measuring beam, wherein the position values are each provided with a timestamp within a measurement period. An evaluation unit is designed to ascertain a surface shape and to ascertain a displacement function, wherein the displacement function represents a movement sequence during the measurement period, and wherein the surface shape and the displacement function are ascertained in such a way that the position values are approximated by the surface shape when the surface shape is moved according to the displacement function.

The measurement system can be refined using further features which are described in the context of the method according to the invention. The method can be refined using further features which are described in the context of the measurement system according to the invention.

BRIEF DESCRIPTION OF THE DRAWINGS

The invention is described by way of example hereinafter with reference to the appended drawings on the basis of advantageous embodiments. In the figures.

DETAILED DESCRIPTION

Figure 1:
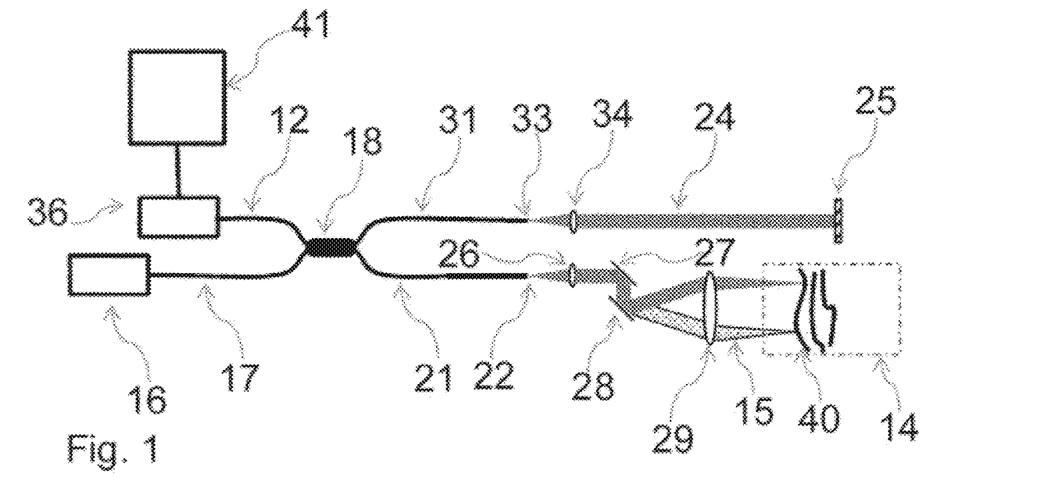
FIG. 1: shows a schematic illustration of a measurement system according to the invention.

A measurement object 14 in the form of a human eye is scanned using an OCT measurement system shown in FIG. 1. In that OCT light 15 is oriented on the measurement object 14, an item of image information is obtained which extends along the axis of the OCT beam into the depths of the measurement object 14 (A-scan). In that the OCT beam is scanned in a direction perpendicular thereto over the measurement object 14, a three-dimensional image of the measurement object 14 can be compiled from a plurality of A-scans. During the time span which the scanning of the eye occupies, the eye can move, which can have a negative effect on the quality of the image information.

The OCT system comprises an OCT light source 16, which is designed as a swept source light source. The swept source light source 16 generates narrowband light which is spectrally tunable. At each moment, narrowband light is thus emitted, the frequency of which changes with time, so that the swept source light source is tuned over a frequency range during a tuning time.

The OCT light 15 emitted by the OCT light source 16 is fed into a first light guide 17, which extends to a fiber coupler 18. In the fiber coupler 18, the OCT light 15 from the first light guide 17 is split into an object beam path 23 and a reference beam path 24. The object beam path 23 extends along an object arm up to the measurement object 14. The reference beam path 24 extends along a reference arm up to a reference mirror 25.

The object arm comprises a second light guide 21, which extends from the fiber coupler 18 up to an exit end 22. At the exit end 22, the object beam path 23 exits in the divergence state from the second light guide 21 and is brought into a collimated state using a collimation lens 26.

A scanning device comprises two scanning mirrors 27, 28, which are pivotable around two axes orthogonal to one another. The object beam path 23 is conducted via the scanning device 27, 28 to an objective 29. The object beam path 23 passes through the objective 29 and is focused in the region of the measurement object 14.

The direction at which the object beam path 23 is incident on the objective 29 changes by pivoting the scanning mirrors 27, 28. Since the second scanning mirror 28 is arranged in the focal point of the objective 29, the beam path 23 extends between the objective 29 and the measurement object 14 independently of the position of the scanning device 27, 28 parallel to the optical axis of the objective 29.

OCT light reflected from the measurement object 14 moves with opposite propagation direction along the object arm 19 back to the fiber coupler 18.

The reference arm comprises a third light guide 31, which extends from the fiber coupler 18 via a second polarization plate 32 up to an exit end 33. The reference beam path 24 exiting in the divergent state from the exit end 33 is incident on a collimation lens 34. From the collimation lens 34, the reference beam path 24 propagates in the collimated state up to the reference mirror 25. The OCT light reflected from the reference mirror 25 runs with opposite propagation direction along the reference arm 20 back to the fiber coupler 18.

The reference mirror 25 is arranged so that the optical path between the fiber coupler 18 and the reference mirror 25 in the reference arm 20 is of equal length to the optical path in the object arm 19 between the fiber coupler 18 and a reference point in the measurement object 14. Since the OCT light has covered the same optical path along the object arm 19 and the reference arm 20, an interference signal results when the object beam path 23 and the reference beam path 24 are brought together again in the fiber coupler 18. The interference signal is stronger the more OCT light is reflected from a specific structure inside the measurement object 14. Scattering centers inside the measurement object 14 can be identified by evaluating the interference signal.

If a scattering center is arranged precisely at the reference point of the object beam path, the optical path of the object beam path 23 and the reference beam path 24 are thus exactly equal in length, so that a standing interference signal results. If the scattering center is remote from the reference point, the interference signal thus oscillates (in spectral representation), wherein the frequency is greater the greater the distance to the reference point is.

The interference signal is conducted to a detector 36 via a fourth light guide 12. The interference signal is recorded using the detector 36 and converted into a location-resolved item of image information.

Figure 2:
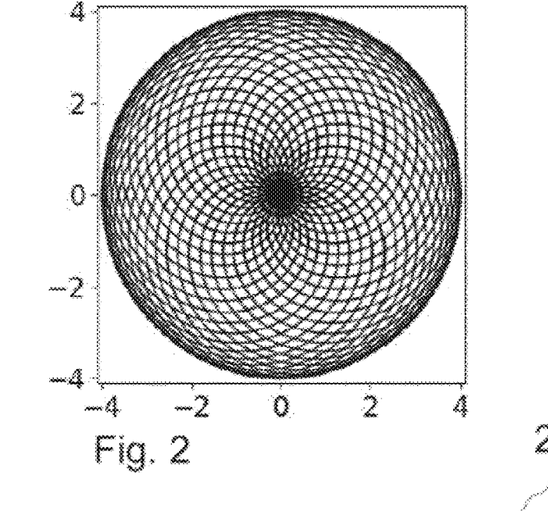
FIG. 2: shows a scanning curve according to the invention.

FIG. 2 shows a curve along which the measuring beam 15 moves in the X direction and in the Y direction under the control of the scanning device 27, 28 relative to the eye 14. The radius of the circle scanned in FIG. 2 is 4 mm. The cornea of a human eye can be covered by a circle diameter of 8 mm.

Figure 3:
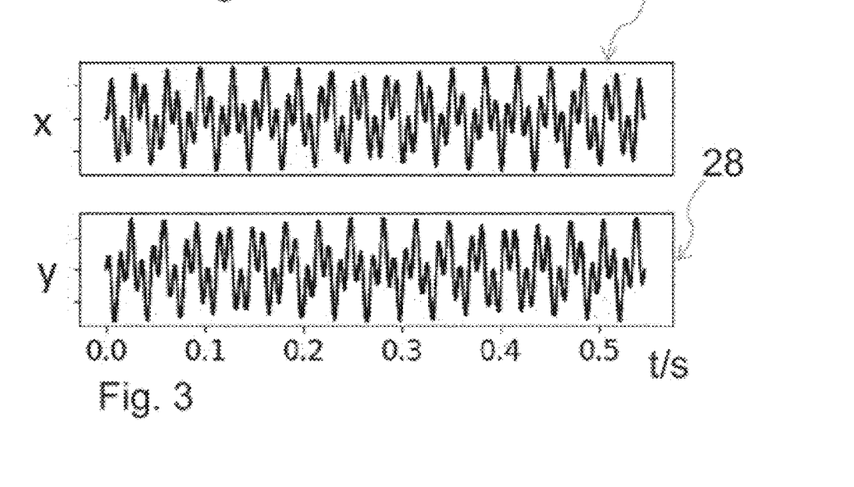
FIG. 3: shows the deflection associated with FIG. 2 of the scanning device in the X direction and Y direction.

The curve according to FIG. 2 can be traversed by the measuring beam 15 in that the scanning device 27, 28 is actuated in the X direction and in the Y direction according to the curves shown in FIG. 3. The actuation takes place according to the following function, the parameters of which are explained in greater detail above.

$$P_{SP}(t) = \begin{pmatrix} x_{SP}(t) \\ y_{SP}(t) \end{pmatrix} = R_{SP} \sin(a \omega t) \begin{pmatrix} \sin(b \omega t) \\ \cos(b \omega t) \end{pmatrix}$$

This curve has the advantage that it can be traversed rapidly, since abrupt direction changes of the scanning mirrors 27, 28 are avoided. A single pass of the curve extends over 0.546 seconds.

If the A-scans are recorded at a frequency of 30 kHz, 16 384 A-scans thus result per pass of the curve shown in FIG. 2. In the present exemplary embodiment, the curve is passed through four times to record a set of position values, so that a total of 65 536 A-scans are recorded, wherein the measurement extends over a duration of 2.184 seconds.

Figure 6:
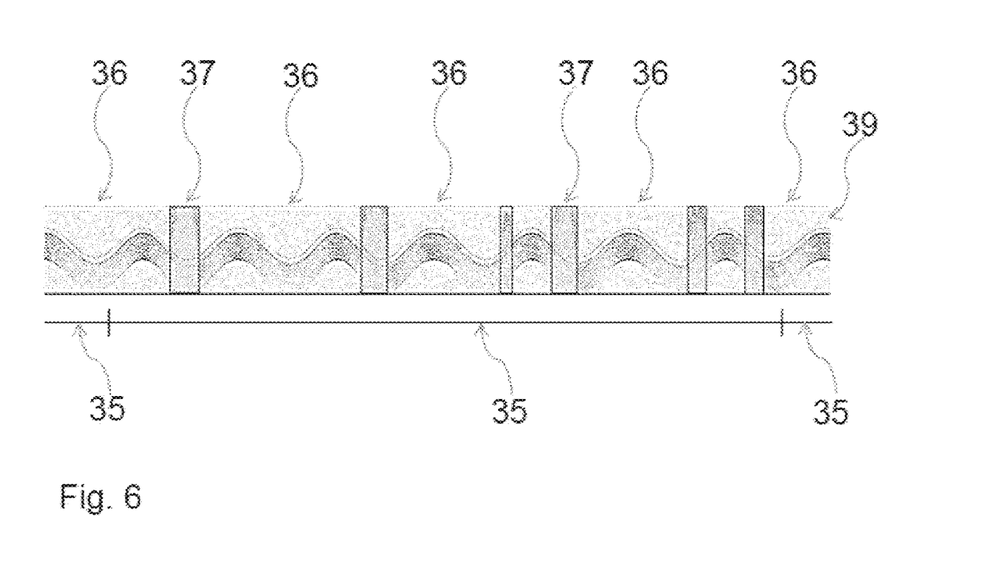
FIG. 6: shows a graphic representation of a set of position values.

The image information ascertained during a measurement using the detector 36 is graphically represented in FIG. 6, in that some of the 65 536 A-scans are arranged adjacent to one another so that a continuous sectional image results.

The measurement is divided into 16 chronologically successive chunks 35, of which one is shown completely and two adjacent ones are shown partially in FIG. 6.

In the measurement, there are large sections 36 having plausible measured values and smaller sections 37 having implausible measured values, in which the eye is covered by the eyelid. The measured values of the implausible sections 37 are deleted from the chunks 35. A reduced number of A-scans remains, in each of which an item of location information about the position of the cornea surface in the Z direction can be inferred. Together with the position of the measuring beam 15 in the X direction and Y direction, a set of position values of the cornea surface results.

Using the method according to the invention, a surface shape and a displacement function 38 in the form of a piecemeal polynomial are ascertained from the position values. The individual method steps for ascertaining the displacement function 38 and the surface shape are explained in greater detail above. The relationship between the position values of the various chunks 35 are described as a translational displacement by the displacement function 38.

Figures 4, 5:
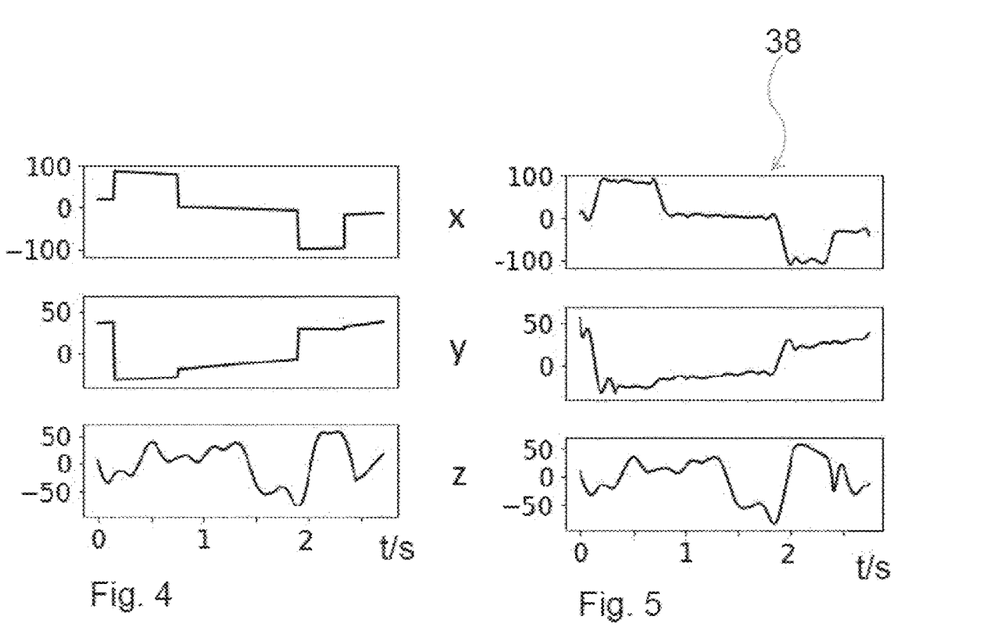
FIG. 4: shows the actual displacement of an object in the X direction, Y direction, and Z direction.
FIG. 5: shows a displacement function associated with FIG. 4, which was ascertained using the method according to the invention.

FIG. 5 shows an example of such a displacement function 38 in the X direction, Y direction, and Z direction. In each of the three graphs arranged one over the other, the translation in micrometers is plotted over the time in seconds. The displacement curve 38 originates from an experiment in which the actual movement of the measurement object 14 had the course shown in FIG. 4. It is shown that the displacements 38 reproduce the actual course of the movement well.

It can be read from the displacement function 38 in which way the eye was displaced translationally during the recording of the position values. The position values can be displaced relative to one another according to the displacement function so that the translation ascertained by the displacement function 38 is compensated for. A movement-corrected set of position values results, which describes the surface of the cornea.

The topography of the cornea can be reconstructed with a higher-order Zernike reconstruction (for example 10th order) from this set of position values. Movement-corrected sectional images can be calculated, or other eye structures, for example the eye lens, can be measured free of movement.

The invention claimed is:
1. A method for performing a movement correction when measuring a human eye, having the following steps:
   a. scanning the eye using a measuring beam to obtain a set of position values of the eye structure, wherein the scanning extends over a measurement period and wherein the position values are each provided with a timestamp within the measurement period;
   b. ascertaining a surface shape and ascertaining a displacement function, wherein the displacement function represents a movement sequence during the measurement period, and wherein the surface shape and the displacement function are ascertained in such a way that the position values are approximated by the surface shape when the surface shape is moved according to the displacement function.

2. The method of claim 1, wherein the position values are corrected on the basis of the displacement function.

3. The method of claim 1, wherein a movement-corrected topography of the cornea is ascertained.

4. The method of claim 1, wherein the shape of the eye structure is represented by a sum of Zernike polynomials.

5. The method of claim 4, wherein the coefficients of the displacement function and the coefficients of the Zernike polynomials are ascertained by solving a uniform optimization task.

6. The method of claim 1, wherein the displacement function is a concatenation of section functions, wherein each section function is a time-dependent polynomial.

7. The method of claim 1, wherein the set of position values is divided into a plurality of chronologically successive chunks and position values of the entire examined eye structure are contained in each chunk.

8. The method of claim 5, wherein the optimization task is regularized in that the displacement function is assumed to be continuous and/or continuous in the first derivative between adjacent section functions.

9. The method of claim 1, wherein the measuring beam is an OCT measuring beam.

10. The method of claim 1, wherein the measuring beam is scanned along a curve over the eye structure, wherein the curve has at least 50, preferably at least 100, more preferably at least 400 intersection points.

11. The method of claim 10, wherein the measuring beam is scanned along the curve multiple times.

12. A measurement system having a measuring beam and a scanning device to deflect the measuring beam in the lateral direction, having a detector, which provides a set of position values of an eye structure from a signal generated by the measuring beam, wherein the position values are each provided with a timestamp within a measurement period, and having an evaluation unit, which is designed to ascertain a surface shape and to ascertain a displacement function, wherein the displacement function represents a movement sequence during the measurement period, and wherein the surface shape and the displacement function are ascertained in such a way that the position values are approximated by the surface shape when the surface shape is moved according to the displacement function.

* * * * *